United States Patent [19]

Spaziante et al.

[11] 4,391,758

[45] Jul. 5, 1983

[54] PROCESS FOR METHYL ISOCYANATE PRODUCTION

[76] Inventors: Placido M. Spaziante, 7, Via San Michele, 6900 Lugano, Switzerland; Luigi Giuffre, Via Passo di Fargorida 6, Milan, Italy

[21] Appl. No.: 369,549

[22] Filed: Apr. 19, 1982

[51] Int. Cl.³ ............................................ C07C 118/00
[52] U.S. Cl. ................................. 260/453 P; 564/73
[58] Field of Search ....................... 260/453 P; 564/73

[56] References Cited

U.S. PATENT DOCUMENTS

| | | | |
|---|---|---|---|
| 3,440,268 | 4/1969 | Stamm | 260/453 P |
| 3,644,461 | 2/1972 | Rennells | 260/453 P |
| 3,852,317 | 12/1974 | Zanker | 260/453 P |
| 3,860,623 | 1/1975 | Zanker et al. | 260/453 P |
| 4,146,550 | 3/1979 | Reichmann et al. | 260/453 P |

Primary Examiner—Dolph H. Torrence
Attorney, Agent, or Firm—Hammond & Littell, Weissenberger and Muserlian

[57] ABSTRACT

An improved process for the preparation of methyl isocyanate comprising reacting methyl carbamoyl chloride with an acid acceptor selected from the group consisting of 1,3-dimethylurea, urea, alkyl ureas and biuret in an organic solvent in which the acid acceptor is soluble but in which the hydrochloride salt thereof is insoluble, separating the acid acceptor hydrochloride from the liquid phase, recovering methyl isocyanate by distillation from the liquid phase, and thermally decomposing acid acceptor hydrochloride to at least a partially free acid acceptor which can preferably be used as a starting material for the production of methyl isocyanate.

18 Claims, 1 Drawing Figure

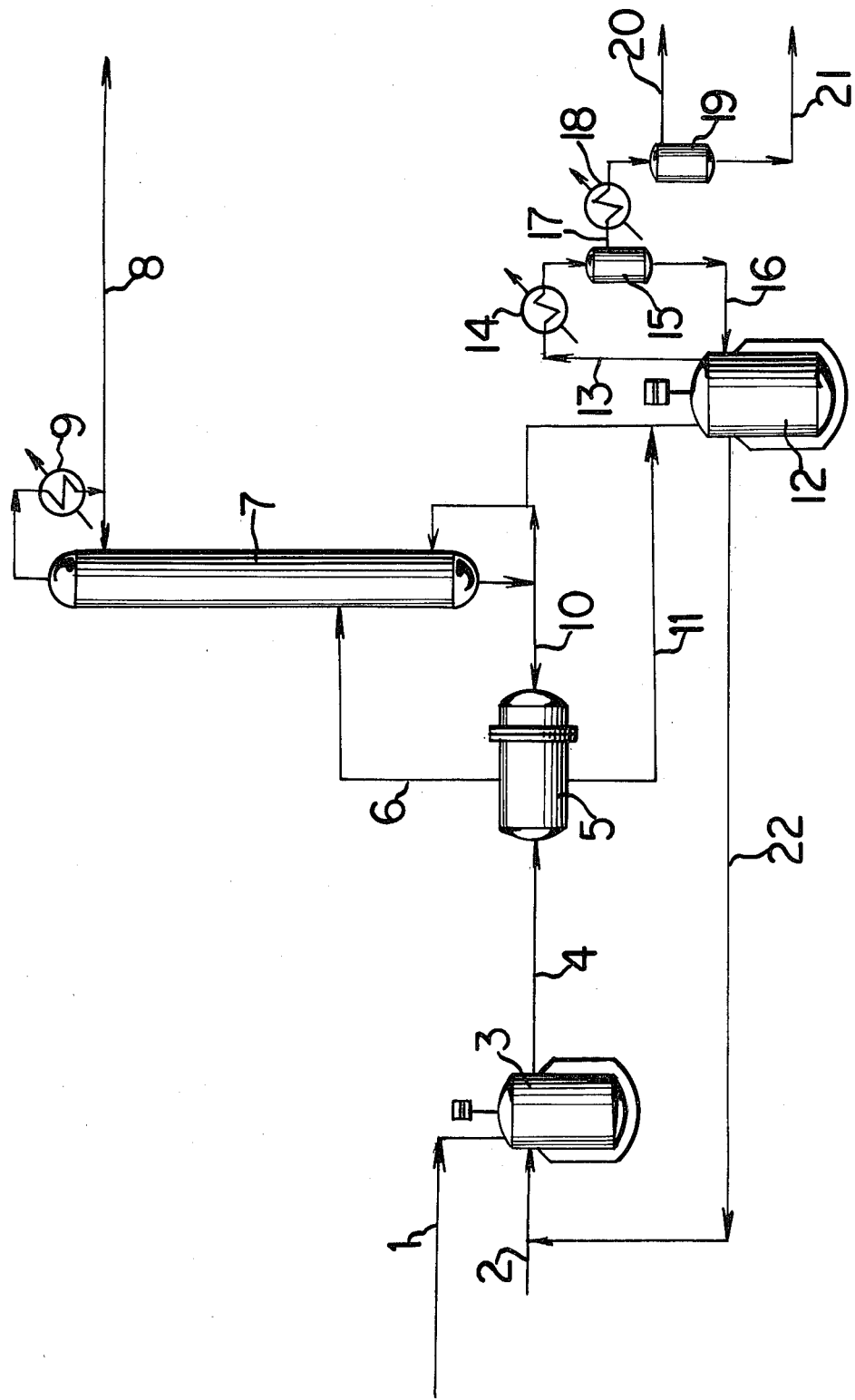

PROCESS FOR METHYL ISOCYANATE PRODUCTION

STATE OF THE ART

Most commercial processes for the production of methyl isocyanate comprise the reaction of methylamine and phosgene in the gaseous phase to form methyl isocyanate and hydrogen chloride and the reaction products are quenched in an organic solvent to form a solution of methylcarbamoyl chloride. An excess of phosgene is required to prevent formation of methylamine hydrochloride in the gaseous phase and the excess phosgene has to be separated from the quench solvent and recycled. About half of the hydrochloric acid formed passes through the quench solvent while the remainder is absorbed in the quench solvent along with methyl isocyanate and continues to form methylcarbamoyl chloride dissolved in the quench solvent.

Excess hydrogen chloride is separated from the quench solvent by appropriate means such as distillation of the methylcarbamoyl chloride solution which leads to decomposition thereof as the temperature rises according to the equilibrium reaction.

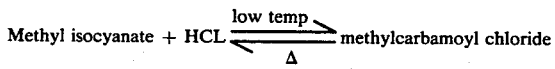

Carbamoyl chloride therefor is assumed to be the product present when methyl isocyanate and hydrogen chloride are present at low temperatures. The presence of hydrogen chloride under these conditions catalyzes the side reaction of polymerization of methyl isocyanate and expensive polymerization inhibitors must be added to the reaction mixture to avoid this unwanted side reaction.

Other known processes use chemical compounds having acidic hydrogen atoms to form an adduct by reaction with methylcarbamoyl chloride which releases hydrogen chloride and is heated to decompose the adduct and to recover methyl isocyanate in a separate step. Such compounds include phenols, substituted phenols and sulfonamides. Other known processes use strong bases such as tetramethylurea or N,N-dimethylaniline to remove hydrogen chloride from methylcarbamoyl chloride by salt formation which are regenerated by treatment with an alkali metal hydroxide such as sodium hydroxide.

Copending U.S. patent application Ser. No. 195,648 filed Oct. 9, 1980 describes a liquid phase process for the preparation of methyl isocyanate by reacting under pressure methylamine hydrochloride with phosgene in a suitable solvent to form methylcarbamoyl chloride, reacting the latter with 1,3-dimethylurea to form methyl isocyanate and 1,3-dimethylurea hydrochloride. The latter compound may be treated to recover methylamine hydrochloride and 1,3-dimethylurea which can be recycled. While the said process has advantages over the gaseous phase reactions, the process has the disadvantages of using undesirable solvents such as chloroform and using phosgene under pressure.

OBJECTS OF THE INVENTION

It is an object of the invention to provide an economical process for producing methyl isocyanate at low pressures and with high yields.

It is another object of the invention to provide a novel method of thermally decomposing 1,3-dimethylurea hydrochloride to 1,3-dimethylurea which can be recycled as a starting material for methyl isocyanate.

These and other objects and advantages of the invention will become obvious from the following detailed description.

THE INVENTION

The novel process of the invention for the production of methyl isocyanate comprising reacting methylcarbamoyl chloride with at least a stoichiometric amount of an acid acceptor selected from the group consisting of 1,3-dimethylurea, urea, alkyl ureas and biuret in an organic solvent in which the acid acceptor is soluble but in which the hydrochloride salt thereof is insoluble, separating the acid acceptor hydrochloride from the liquid phase and recovering methyl isocyanate by distillation from the liquid phase.

The reaction of the acid acceptor, preferably 1,3-dimethylurea, and methylcarbamoyl chloride results in a solid-liquid phase mixture with methyl isocyanate remaining in solution and the 1,3-dimethylurea—HCl or other acid acceptor hydrochloride precipitating out so that it can be easily recovered by filtration or other suitable means. The methyl isocyanate solution is then subjected to distillation to separate the methyl isocyanate from the solvent.

In the prior art method using N,N,N',N'-tetramethylurea as a reactant in place of 1,3-dimethylurea under the same conditions and in the same solvent such as chlorobenzene, there is no two phase formation as both the tetramethylurea hydrochloride and methyl isocyanate are soluble therein. This means it's not possible to separate the two compounds in an efficient manner.

In a preferred continuous embodiment of the process of the invention, the methyl isocyanate preparation comprises reacting methylcarbamoyl chloride with at least a stoichiometric amount of 1,3-dimethylurea in an organic solvent in which 1,3-dimethylurea hydrochloride is insoluble, separating the 1,3-dimethylurea hydrochloride from the liquid phase and recovering methyl isocyanate by distillation from the liquid phase, subjecting a slurry of 1,3-dimethylurea hydrochloride and the solvent to thermal decomposition at a temperature of from about 50° C. to about the boiling point of the solvent and preferably at 80° to 95° C. preferably under reduced pressure whereby hydrogen chloride gas is removed and a mixture of 1,3-dimethylurea and 1,3-dimethylurea hydrochloride is formed and recycling the said mixture to the first step for reaction with methylcarbamoyl chloride.

The thermal decomposition temperature of 1,3-dimethylurea hydrochloride is from about 50° C. to the boiling point of the solvent, preferably from about 80° to 95° C. Solvent recovered after distillation of methyl isocyanate therefrom may be recycled to the filtration stage. The hydrogen chloride gas produced in the dimethylurea decomposition may be recovered.

A crucial step in the continuous process and one which is an object of the invention is the thermal regeneration of 1,3-dimethylurea from 1,3-dimethylurea hydrochloride in good yields without side reactions and without the use of a strong base to neutralize the acid salt. The use of a strong base is expensive and requires another operation to remove the salt formed in the neutralization step which the step of the invention avoids.

The temperature range of 80° to 95° C. is preferred for the recovery of dimethylurea from dimethylurea hydrochloride. At temperatures below 80° C., the thermal decomposition according to the following reaction is slow

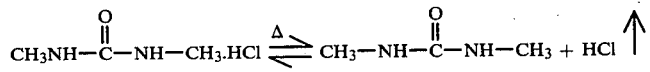 

At temperatures above 95° C., there is loss of some 1,3-dimethylurea due to the following side reaction

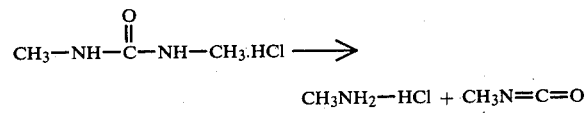

The thermal decomposition is preferably not completely effected for economical reasons and it has been found that if the thermal decomposition produces about a 50—50 mixture of 1,3-dimethylurea and 1,3-dimethylurea hydrochloride, the mixture can easily be recycled to the step for reaction with methylcarbamoyl chloride.

The organic solvent used in the process of the invention is an organic solvent in which the acid acceptor such as methyl isocyanate is soluble and its hydrochloride such as 1,3-dimethylurea hydrochloride is insoluble for easy separation of the two reaction products. Examples of suitable solvents are aromatic hydrocarbons and halogenated aromatic hydrocarbons, such as toluene, xylene, benzene, other alkyl benzenes, monochlorobenzenes, dichlorobenzenes and other halogenated benzenes or halogenated alkyl benzenes. Especially preferred as a solvent is chlorobenzene since it not only has the desirable solubility properties, it has a boiling point higher than the preferred thermal decomposition range of 1,3-dimethylurea hydrochloride of 80° to 95° C. Only a small amount vaporizes under these conditions and therefor need not be recovered.

The reaction of 1,3-dimethylurea and methylcarbamoyl chloride may be effected at temperatures of 10° to 50° C. but is preferably effected at 30° to 40° C. At temperatures below 30° C., the reaction is rather slow and at temperatures above 40° C., the methyl isocyanate formed will undergo side reactions such as the formation of biuret thereby decreasing the yields of the desired product. Preferably, the reaction mixture contains a slight excess of 1,3-dimethylurea.

The properties of the hydrogen chloride acceptor compounds that are useful in this process are that they remove HCl from methylcarbamoyl chloride by forming a hydrochloride salt and methyl isocyanate at the initial reaction temperature below about 200° C. and which decompose into hydrogen chloride and the original acceptor compound, without generating reaction side products, when heated to about 10° C. to about 100° C. above the temperature of the initial reaction forming methyl isocyanate. They should be relatively nonvolatile at the temperature at which the hydrogen chloride decomposition takes place. It is further desirable that the hydrogen chloride acceptor compound be soluble in the solvent while its hydrochloride salt be insoluble in the same solvent at the reaction temperature at which the methyl isocyanate forms 1,3-dimethylurea is a hydrogen chloride acceptor that meets these criteria and by adjustment of solvent, reaction conditions, and decomposition conditions, such compounds such as urea, other 1,3-dialkylureas of 1 to 7 alkyl carbon atoms and biuret, are also suitable hydrochloric acid acceptors.

Referring now to the drawing:

The FIG. 1 is a schematic flow sheet of the preferred continuous process of the invention for the preparation of methyl isocyanate.

A solution of carbamoyl chloride in a suitable solvent such as chlorobenzene is introduced by line 1 into reactor 3 and a slight excess of 1,3-dimethylurea in chlorobenzene usually containing some 1,3-dimethylurea hydrochloride in chlorobenzene is added by line 2 to reactor 3 which is operated at 30° to 40° C. A slurry of 1,3-dimethylurea hydrochloride (solid phase) and methyl isocyanate in chlorobenzene (liquid phase) is formed and the slurry is removed by line 4 to filter 5. The liquid phase from the filter is removed by line 6 to distillation column 7 wherein the solution is distilled to remove methyl isocyanate by line 8 after condensation in condensor 9. The chlorobenzene solvent from distillation column 7 is passed by line 10 to wash the filter and obtain a slurry of chlorobenzene and 1,3-dimethylurea hydrochloride.

The said slurry is passed by line 11 to thermal reactor 12 wherein the said slurry is heated to decompose the said hydrochloride salt at 80° to 95° C. The hydrogen chloride gas containing some chlorobenzene vapor mixture with traces of 1,3-dimethylurea is removed by line 13 to condensor 14 operated at 60° C. to condense the residual chlorobenzene and traces of dimethylurea which are separated in separator 15 and returned by line 16 to the reactor 12. The gaseous mixture of hydrogen chloride and chlorobenzene from separator 15 is passed by line 17 through condensor 18 and then to separator 19. Gaseous hydrogen chloride is recovered by line 20 and liquid chlorobenzene is recovered by line 21 and may be readded to the process at an appropriate place.

The result of the thermal decomposition in reactor 12 is a mixture of 1,3-dimethylurea and 1,3-dimethylurea hydrochloride in chlorobenzene since the thermal decomposition is not complete and it has been ascertained that a 1—1 mixture is best maintained in reactor 12 since this gives a single liquid phase which is removed by line 22 and is recycled to line 2 for addition to reactor 3.

In the following example there are described several preferred embodiments of the invention but it should be understood that the invention is not intended to be limited to the specific embodiments.

EXAMPLE

The present example is discussed in connection with with plant flow sheet illustrated in the figure for the production of 5,000 metric tons of methyl isocyanate per year. A solution of 1035 kg of methylcarbamoyl chloride is 4509 kg of chlorobenzene is introduced each hour into reactor 3 by line 1 and a solution of 975 kg of 1,3-dimethylurea, 1379 kg of 1,3-dimethylurea hydrochloride and 1926 kg of chlorobenzene per hour is added to reactor 3 by line 2. A slurry of 631 kg of methyl isocyanate, 2758 kg of 1,3-dimethylurea hydrochloride and 6435 kg of chlorobenzene per hour is passed by line 4 from the reactor 3 to filter 5. The liquid phase from filter 5 containing 631 kg of methyl isocyanate in 9193 kg of chlorobenzene per hour is passed by line 10 to wash the filter and from a mixture of 2758 kg of 1,3-dimethylurea hydrochloride in 6435 kg of chlorobenzene which is passed by line 11 to thermal decomposer 12. There is recovered from reactor 12 404 kg per hour of gaseous hydrogen chloride which may be recovered by absorption and 4509 kg per hour of chlorobenzene. The solution of a mixture of about 1:1 1,3-dimethylurea and 1,3-dimethylurea hydrochloride in chlorobenzene is passed by line 22 to the start of the process.

Various modifications of the processes of the invention may be made without departing from the spirit or scope thereof and it is to be understood that the invention is intended to be limited only as defined in the appended claims.

We claim:

1. A process for the preparation of methyl isocyanate comprising reacting methylcarbamoyl chloride with about a stoichiometric amount of an acid acceptor selected from the group consisting of dimethylurea, urea, alkyl ureas and biuret in an organic solvent in which said acid acceptor is soluble and in which the hydrochloride salt of said acid acceptor is insoluble, separating the acid acceptor hydrochloride from the liquid phase, recovering methyl isocyanate by distillation from said liquid phase, and thermally decomposing said acid acceptor hydrochloride salt to regenerate said acid acceptor.

2. The process of claim 1 wherein the acid acceptor is 1,3-dimethylurea and wherein the solvent is selected from the group consisting of toluene, xylene, benzene, and chlorinated benzenes and alkyl benzenes.

3. The process of claim 2 wherein the solvent is chlorobenzene.

4. The process of claim 2 wherein the reaction of methylcarbamoyl chloride and 1,3-dimethylurea is effected at 30° to 40° C.

5. The process of claim 2 or 4 wherein there is a slight excess of 1,3-dimethylurea.

6. A continuous process for the preparation of methyl isocyanate comprising reacting methylcarbamoyl chloride with 1,3-dimethylurea in an organic solvent in which the 1,3-dimethylurea is soluble and in which the 1,3-dimethyl hydrochloride is insoluble, separating the 1,3-dimethyl hydrochloride from the liquid phase, recovering methyl isocyanate by distillation from the liquid phase, subjecting a slurry of 1,3-dimethylurea hydrochloride and the organic solvent to thermal decomposition whereby hydrogen chloride gas is removed leaving a mixture of 1,3-dimethylurea and 1,3-dimethylurea hydrochloride and recycling said latter mixture to the first step for reaction with methylcarbamoyl chloride.

7. A process as set forth in claim 6 wherein the solvent 1,3-dimethyl chloride salt slurry is subjected to thermal decomposition at a temperature in the range from about 80° to about 95° C.

8. The process of claim 6 wherein the solvent is chlorobenzene.

9. The process of claim 6 wherein the reaction of methylcarbamoyl chloride and 1,3-dimethylurea is effected at 30° to 40° C.

10. The process of claim 6 wherein there is a slight excess of 1,3-dimethylurea.

11. The process of claim 6 wherein the thermal decomposition mixture recycled to the first step is a solution of about a 1:1 mixture of 1,3-dimethylurea and a 1,3-dimethylurea hydrochloride.

12. The process of claim 8 wherein the thermal decomposition is effected at 85° to 90° C. and at a pressure at which the solvent chlorobenzene refluxes.

13. A process for thermal decomposition of 1,3-dimethylurea hydrochloride comprising heating at 80° to 95° C. a solution of 1,3-dimethylurea hydrochloride in an organic solvent under reduced pressure while removing hydrogen chloride gas.

14. The process of claim 13 wherein the organic solvent is chlorobenzene.

15. The process of claim 14 wherein the reaction is effected at 85° to 90° C. at a reduced pressure at which chlorobenzene is at reflux.

16. A process for the preparation of methyl isocyanate comprising reacting methylcarbamoyl chloride with at least a stoichiometric amount of 1,3-dimethylurea in an organic solvent in which 1,3-dimethylurea hydrochloride is insoluble, separating the 1,3-dimethylurea hydrochloride from the liquid phase and recovering methyl isocyanate by distillation from the liquid phase.

17. The process of claim 1 wherein the solvent is chlorobenzene.

18. The process of claim 1 wherein the reaction of methylcarbamoyl chloride and 1,3-dimethylurea is effected at 30° to 40° C.

* * * * *